US006905749B2

United States Patent
Fukuzawa

(12) United States Patent
(10) Patent No.: US 6,905,749 B2
(45) Date of Patent: Jun. 14, 2005

(54) OPTICAL RECORDING DISK, METHOD FOR MAKING AND USING THE SAME

(75) Inventor: Narutoshi Fukuzawa, Tokyo (JP)

(73) Assignee: TDK Corporation, Tokyo (JP)

( * ) Notice: Subject to any disclaimer, the term of this patent is extended or adjusted under 35 U.S.C. 154(b) by 0 days.

(21) Appl. No.: 10/712,309

(22) Filed: Nov. 12, 2003

(65) Prior Publication Data

US 2004/0142138 A1 Jul. 22, 2004

Related U.S. Application Data

(63) Continuation-in-part of application No. 10/705,815, filed on Nov. 10, 2003.

(51) Int. Cl.$^7$ ................................................ B32B 3/02
(52) U.S. Cl. .................... 428/64.1; 428/64.4; 428/64.8; 430/270.16
(58) Field of Search ............................. 428/64.1, 64.4, 428/64.8; 430/270.14, 270.16, 945.1

(56) References Cited

U.S. PATENT DOCUMENTS

| | | | | |
|---|---|---|---|---|
| 4,908,442 A | * | 3/1990 | Narang et al. ............... | 540/145 |
| 4,950,579 A | * | 8/1990 | Debe et al. ............. | 430/270.16 |
| 5,064,952 A | * | 11/1991 | Chang et al. ............... | 540/145 |
| 5,087,390 A | * | 2/1992 | Sounik et al. ............... | 252/587 |
| 5,658,707 A | * | 8/1997 | Takuma et al. ........ | 430/270.15 |
| 5,871,882 A | * | 2/1999 | Schmidhalter et al. . | 430/270.16 |
| 6,576,321 B2 | * | 6/2003 | Mihara et al. ............. | 428/64.1 |
| 2003/0118937 A1 | * | 6/2003 | Nara et al. ............. | 430/270.16 |

FOREIGN PATENT DOCUMENTS

| | | |
|---|---|---|
| JP | 01-174488 | 7/1989 |
| JP | 06-295469 | 10/1994 |
| JP | 08-127174 | 5/1996 |
| JP | 11-058965 | 3/1999 |
| JP | 11-221964 | 8/1999 |
| JP | 11-334207 | 12/1999 |
| JP | 2001-138633 | 5/2001 |
| JP | 2001-287462 | 10/2001 |
| JP | 2001-287465 | 10/2001 |

* cited by examiner

Primary Examiner—Elizabeth Mulvaney
(74) Attorney, Agent, or Firm—Seed IP Law Group PLLC

(57) ABSTRACT

An optical recording disk includes at least a recording layer containing an organic compound containing a porphyrin system dye as a primary component and a light transmission layer which transmits a laser beam having a wavelength of 390 to 420 nm on a support substrate in this order, the porphyrin system dye having a minimal value $n_{min}$ of a refractive index n within a wavelength region of 390 nm to 420 nm and a refractive index n equal to or lower than 1.2 with respect to the laser beam having the wavelength of 390 to 420 nm and absorbing the laser beam having the wavelength of 390 to 420 nm to be melted or decomposed, whereby the refractive index thereof changes and data are recorded in the optical recording disk.

According to the thus constituted optical recording disk, it is possible to record data therein using a bluish-violet laser beam having a wavelength of 390 to 420 nm and reproduce data therefrom using a bluish-violet laser beam having a wavelength of 390 to 420 nm.

39 Claims, 1 Drawing Sheet

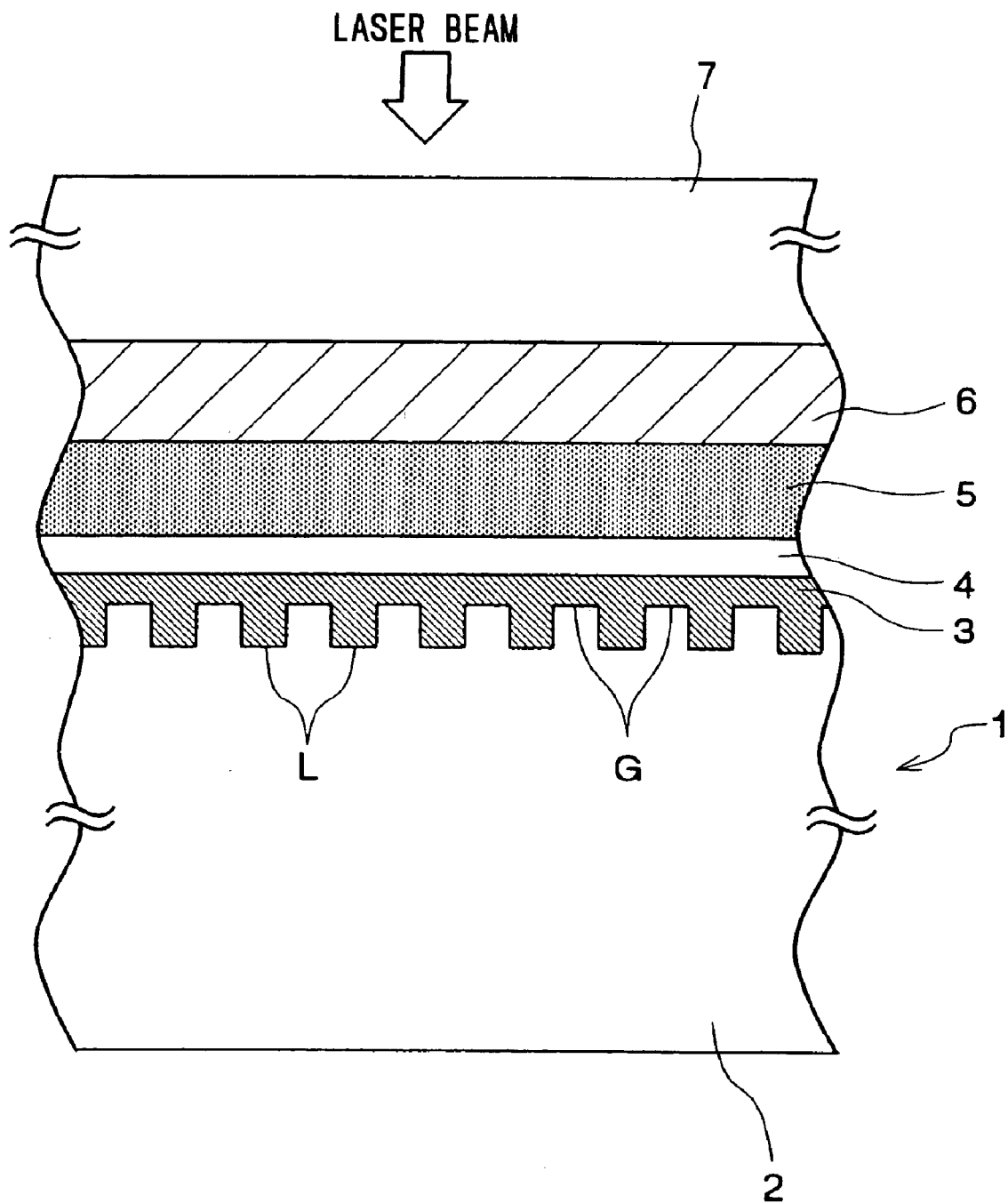

OPTICAL RECORDING DISK, METHOD FOR MAKING AND USING THE SAME

CROSS-REFERENCE TO RELATED APPLICATIONS

This application is a continuation-in-part of U.S. patent application entitled "OPTICAL RECORDING DISK, METHOD FOR MANUFACTURING OPTICAL RECORDING DISK AND OPTICAL RECORDING AND REPRODUCING METHOD FOR OPTICAL RECORDING DISK" U.S. patent application Ser. No. 10/705,815 filed Nov. 10, 2003, which claims priority to Japanese Patent Application No. 2002-327258, filed Nov. 11, 2002, all of which are incorporated herein by reference in their entirety.

TECHNICAL FIELD

The present invention relates to an optical recording disk, a method for manufacturing an optical recording disk and an optical recording and reproducing method and, particularly, to an optical recording disk which includes a recording layer containing an organic compound as a primary component, in which data can be recorded using a bluish-violet laser beam having a wavelength of 390 to 420 nm and from which data can be reproduced using a bluish-violet laser beam having a wavelength of 390 to 420 nm, a method for manufacturing the optical recording disk and an optical recording and reproducing method capable of recording data in and reproducing from an optical recording disk including a recording layer containing an organic compound as a primary component using a bluish-violet laser beam having a wavelength of 390 to 420 nm.

BACKGROUND OF THE INVENTION

Recently, optical recording media such as the CD, DVD and the like have been widely used as recording media for recording a large volume of digital data.

These optical recording media can be roughly classified into so-called ROM type optical recording media such as the CD-ROM and the DVD-ROM that do not enable writing and rewriting of data, so-called write-once type optical recording media such as the CD-R and DVD-R that enable writing but not rewriting of data, and so-called data rewritable optical recording media such as the CD-RW and DVD-RW that enable rewriting of data.

Among these, write-once type optical recording disks such as the CD-R and DVD-R using an organic dye as a material for a recording layer have been widely used.

Since the CD-R in which data can be recorded and from which data can be reproduced using a laser beam having a near-infrared wavelength can prevent unauthorized alteration of recorded information and is low in cost, it is widely accepted in the market.

On the other hand, demand for increased recording density enabling motion picture images to be recorded over a long period of time has led to the development and wide use of a DVD-R in which data can be recorded and from which data can be reproduced using a laser beam of infrared wavelength. Specifically, in the DVD-R, recording capacity (4.7 GB/surface) which is six to eight times that of the CD has been achieved by shortening the wavelength of the laser beam used to record and reproduce data from 780 nm for the CD to 650 nm and increasing the numerical aperture NA of the optical system from 0.45 for the CD to 0.6. The DVD-R can record about two hours of ordinary television signals.

To enable recording of data in optical recording disks at still higher density, the wavelength of the laser beam used for recording and reproducing data has recently been made much shorter and the numerical aperture of the optical system made much larger. This has led to the development of a next-generation type optical recording disk suitable for a system using bluish-violet laser beam having a wavelength of 390 to 420 nm and an objective lens system whose numerical aperture NA is equal to or larger than 0.76. This use of a short wavelength laser beam is expected to markedly increase the recording density of optical recording disks.

Various organic dye materials have been proposed for use in the recording layer of the CD-R and the DVD-R but the only ones that have been put to practical use are those which have an absorption spectrum on the long wavelength side that coincides with the wavelength region of the laser beam used for recording and reproducing data and which have a refractive index n of higher than 2.0 and a suitable extinction coefficient k of higher than 0.01 and lower than 0.10 on the long wavelength side of the absorption spectrum thereof.

When the laser beam for recording and reproducing data is projected onto a recording layer, the organic dye material contained in the recording layer absorbs the laser beam to be melted or decomposed. As a result, the refractive index is greatly changed from a high refractive index to a low refractive index to form a record pit, thereby recording data in the recording layer. When data recorded in the recording layer are to be reproduced, the laser beam for recording and reproducing data is projected onto the recording layer and data are read utilizing the difference in reflective coefficients with respect to the laser beam between the record pit and unrecorded regions around the record pit.

In the CD-R or the DVD-R, a high reflective coefficient is required for compatibility with the CD-ROM or DVD-ROM, because these media have a high reflective coefficient. However, since a high reflective coefficient cannot be achieved using only an organic dye material having a refractive index n higher than 2.0 and an extinction coefficient k higher than 0.01 and lower than 0.10, a metal reflective layer having a high reflective coefficient is provided on the opposite side from the laser beam incidence side with respect to the recording layer. Since the CD-R and DVD-R thus require a high refractive index and a high modulation for compatibility with the ROM, there have come into wide practical use organic dye materials that are melted or decomposed by light having a wavelength within the wavelength region of the laser beam used for recording and reproducing data, thereby enabling the refractive index of the organic dye material to change from a high value to a low value.

In the next-generation type optical recording disk employing a bluish-violet semiconductor laser beam having a wavelength of 390 to 420 nm for recording and reproducing data, it is difficult to increase the reflective coefficient of a data rewritable type optical recording disk using a phase change material as the material for the recording layer to substantially the same level as that of the ROM. The specifications established for the next-generation type optical recording disk therefore designate a low reflective coefficient. Since, unlike in the CD-R or the DVD-R, a high reflective coefficient is not required, it is possible to employ as the material for the recording layer of a write-once type optical recording disk an organic dye material that changes from a low refractive index to a high refractive index when melted or decomposed by irradiation with a laser beam. Japanese Patent Application Laid Open No. 2001-273672 suggests this possibility.

However, no organic dye material has yet been found whose refractive index changes from a low value to a high value when melted or decomposed by irradiation with a laser beam for recording and reproducing data that has a wavelength of 390 to 420 nm.

Further, unlike in the CD-R or the DVD-R, it is difficult to make the long wavelength side of the absorption spectrum of an organic dye material coincide with the wavelength region of 390 to 420 nm.

Furthermore, although ultraviolet ray absorbing agents whose absorption spectrum on the long wavelength side is within the wavelength range of 390 to 420 nm are available, they have a short conjugated system, in other words, are composed of small molecules. Since their solubility in an organic solvent is therefore generally low, these ultraviolet ray absorbing agents are not compatible with the spin coating process and tend to crystallize when used to form a thin film.

SUMMARY OF THE INVENTION

It is therefore an object of the present invention to provide an optical recording disk which includes a recording layer containing an organic compound as a primary component, in which data can be recorded using a bluish-violet laser beam having a wavelength of 390 to 420 nm and from which data can be reproduced using a bluish-violet laser beam having a wavelength of 390 to 420 nm.

It is another object of the present invention to provide a method for manufacturing an optical recording disk which includes a recording layer containing an organic compound as a primary component, in which data can be recorded using a bluish-violet laser beam having a wavelength of 390 to 420 nm and from which data can be reproduced using a bluish-violet laser beam having a wavelength of 390 to 420 nm.

It is a further object of the present invention to provide an optical recording and reproducing method capable of recording data in and reproducing from an optical recording disk including a recording layer containing an organic compound as a primary component using a bluish-violet laser beam having a wavelength of 390 to 420 nm.

The inventors of the present invention vigorously pursued a study for accomplishing the above objects and, as a result, made the discovery that a porphyrin system dye represented by a general formula (1) was melted or decomposed by irradiation with a laser beam having a wavelength of 390 to 420 nm, whereby the refractive index thereof changed from a low value to a high value and a desired carrier/noise ratio and a desired reflective coefficient could be achieved and that since the molar absorbance coefficient thereof with respect to a bluish-violet laser beam was high and the above identified porphyrin system dye had excellent light resistance, the above identified porphyrin system dye had an excellent characteristic as an organic dye for forming a recording layer of a next-generation type optical recording disk.

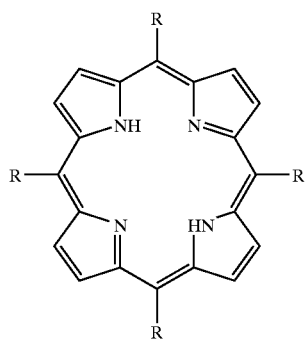

(1)

Therefore, the above and other objects of the present invention can be accomplished by an optical recording disk comprising a recording layer containing an organic compound as a primary component, the organic compound containing a porphyrin system dye represented by general formula (1) as a primary component.

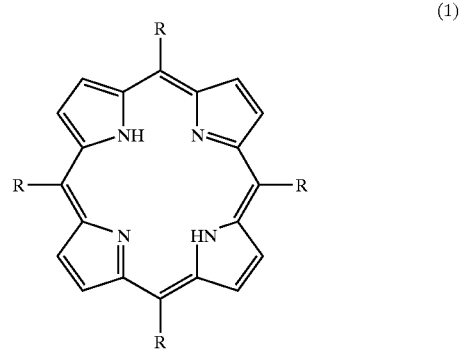

(1)

In a preferred aspect of the present invention, the optical recording disk comprises at least a recording layer containing the organic compound containing the porphyrin system dye as a primary component and a light transmission layer which transmits a laser beam having a wavelength of 390 to 420 nm on a support substrate in this order, the porphyrin system dye having a minimal value $n_{min}$, of a refractive index (real part of complex refractive index) n within a wavelength region of 390 nm to 420 nm and a refractive index n equal to or lower than 1.2 with respect to the laser beam having the wavelength of 390 to 420 nm and the laser beam having the wavelength of 390 to 420 nm to be melted or decomposed, whereby the refractive index thereof changes and data are recorded in the optical recording disk.

In the present invention, it is preferable for the porphyrin system dye to be melted or decomposed by the laser beam, whereby the refractive index n thereof increases.

In the present invention, it is preferable for an extinction coefficient (imaginary part of the complex refractive index) k of the porphyrin system dye to be equal to or higher than 1.5 at wavelengths of a laser beam for reproducing data and a laser bream for recording data. In a preferred aspect of the present invention, each R in the general formula (1) is independently selected from the group consisting of

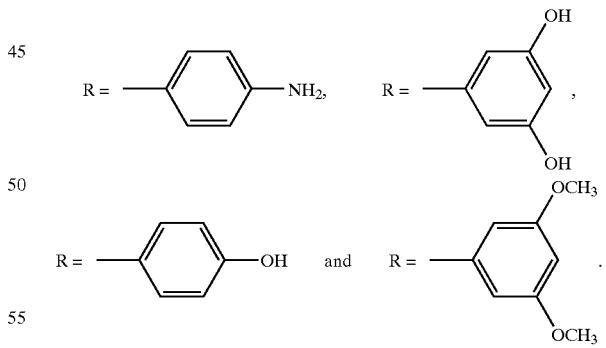

In a preferred aspect of the present invention, the recording layer further contains a ketone system solvent whose carbon number is 5 to 7.

In a further preferred aspect of the present invention, the recording layer further contains a ketone system solvent whose carbon number is 6.

In the present invention, the ketone system solvent may have a chain structure or a ring-shaped structure but a ketone system solvent having a linear chain structure and a branch structure is preferable.

In a preferred aspect of the present invention, the support substrate is formed of a polyolefin resin.

According to this preferred aspect of the present invention, since the support substrate is formed of a polyolefin resin, it is possible to reliably prevent the support substrate from being damaged by a ketone system solvent whose carbon number is 5 to 7.

In a preferred aspect of the present invention, the support substrate is formed of an amorphous polyolefin resin.

In a preferred aspect of the present invention, the optical recording disk further includes a thin film formed of a metal and/or a dielectric material on the support substrate.

In the present invention, the thin film formed of a metal and/or a dielectric material has a thickness of 5 to 70 nm and preferably has a thickness of 10 to 40 nm. Illustrative examples of metals for forming the thin film include Ag and alloy containing Ag as a primary component and illustrative examples of dielectric materials include $Al_2O_3$ and ZnS+$SiO_2$ (mole ratio of 80:20). It is possible to suppress heat influence between neighboring record marks and adjust the reflective coefficient of the optical recording disk by providing such a thin film.

In a preferred aspect of the present invention, the optical recording disk further includes a dielectric film whose refractive index (real part of complex refractive index) n equal to or higher than 1.8 on the support substrate.

In the present invention, the dielectric film has a thickness of 5 to 100 nm and preferably has a thickness of 20 to 70 nm. When the thickness of the dielectric film exceeds 100 nm, the sensitivity of the optical recording disk is undesirably lowered. Illustrative examples of dielectric materials used to form the dielectric film include $CeO_2$+$Al_2O_3$ (mole ratio of 80:20), ZnS+$SiO_2$ (mole ratio of 80:20) and the like. The dielectric film serves to protect the recording layer in the case where the light transmission layer is formed on the recording layer and adjust the reflective coefficient of the optical recording disk and, therefore, if these functions can be achieved by another means, it is not absolutely necessary to provide the dielectric film.

In a preferred aspect of the present invention, the recording layer further contains a quencher.

The above and other objects of the present invention can be also accomplished by a method for manufacturing an optical recording disk comprising steps of dissolving a porphyrin system dye represented by general formula (1) into a ketone whose carbon number is 5 to 7 to prepare a coating solution, and applying the thus prepared coating solution onto a support substrate using a spin coating process to form a recording layer.

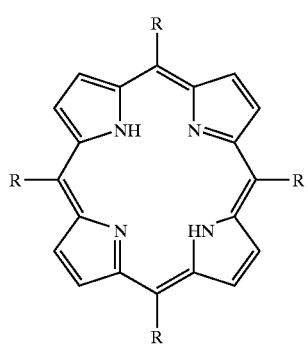

(1)

The inventors of the present invention made the discovery that a porphyrin system dye represented by a general formula (1) was melted or decomposed by irradiation with a laser beam having a wavelength of 390 to 420 nm, whereby the refractive index thereof changed from a low refractive index to a high refractive index and a desired carrier/noise ratio and a desired reflective coefficient could be achieved and that since the molar absorbance coefficient thereof with respect to a bluish-violet laser beam was high and the above identified porphyrin system dye had excellent light resistance, the above identified porphyrin system dye had an excellent characteristic as an organic dye for forming a recording layer of a next-generation type optical recording disk. However, since the solubility of the porphyrin system dye in an organic solvent is low, it was sometimes difficult to prepare a coating solution used for a spin coating process. The inventors of the present invention nevertheless vigorously pursued a study for accomplishing the above objects and, as a result, made the discovery that the porphyrin system dye has high solubility in a ketone system solvent whose carbon number 5 to 7. Therefore, according to the present invention, since the porphyrin system dye is dissolved into a ketone system solvent whose carbon number is 5 to 7, it is possible to prepare a coating solution compatible with a spin coating process and, therefore, an optical recording disk including a recording layer having a high molar absorbance coefficient and excellent light resistance can be manufactured by applying the thus prepared coating solution onto a support substrate using a spin coating process.

In a preferred aspect of the present invention, the method for manufacturing an optical recording disk comprises steps of dissolving the porphyrin system dye having a minimal value $n_{min}$ of a refractive index (real part of complex refractive index) n within a wavelength region of 390 nm to 420 nm and a refractive index n equal to or lower than 1.2 with respect to the laser beam having the wavelength of 390 to 420 nm into a ketone system solvent whose carbon number is 5 to 7, thereby preparing a coating solution, and applying the thus prepared coating solution onto the support substrate using a spin coating process to form a recording layer.

In a further preferred aspect of the present invention, each R in the general formula (1), is independently selected from the group consisting of

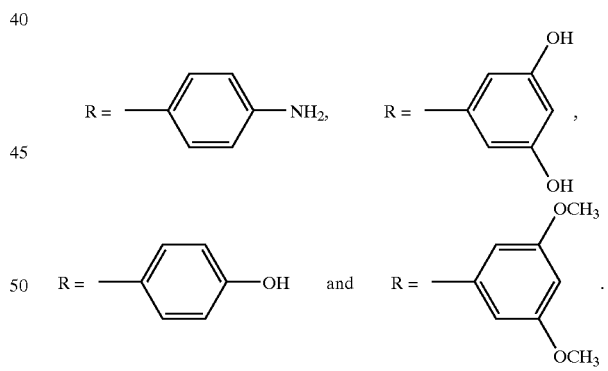

In a further preferred aspect of the present invention, the coating solution is prepared by dissolving the above identified porphyrin system dye into a ketone system solvent whose carbon number is 6.

In the present invention, the ketone system solvent may have a chain structure or a ring-shaped structure but a ketone system solvent having a linear chain structure and a branch structure is preferable.

In a preferred aspect of the present invention, the recording layer is formed by applying the coating solution onto the support substrate formed of a polyolefin resin.

According to this preferred aspect of the present invention, since the support substrate is formed of a polyolefin resin, it is possible to reliably prevent the support substrate from being damaged by a ketone system solvent whose carbon number is 5 to 7.

In a further preferred aspect of the present invention, the recording layer is formed by applying the coating solution onto the support substrate formed of an amorphous polyolefin resin.

The above and other objects of the present invention can be also accomplished by an optical recording and reproducing method for an optical recording disk including at least a recording layer containing an organic compound as a primary component and a light transmission layer which transmits a laser beam having a wavelength of 390 to 420 nm on a support substrate in this order, the organic compound containing a porphyrin system dye represented by general formula (1) as a primary component, the optical recording and reproducing method comprising steps of projecting a laser beam of a wavelength of 390 to 420 nm for recording data onto the recording layer via the light transmission layer, thereby recording data in the recording layer and increasing a refractive index n of the porphyrin system dye with respect to a laser beam of a wavelength of 390 to 420 nm for reproducing data, and projecting the laser beam of a wavelength of 390 to 420 nm for reproducing data onto the recording layer via the light transmission layer, thereby reproducing data recorded in the recording layer.

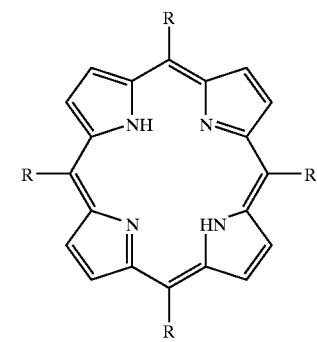

(1)

In a preferred aspect of the present invention, the porphyrin system dye has a minimal value $n_{min}$ of a refractive index (real part of complex refractive index) n within a wavelength region of 390 nm to 420 nm and a refractive index n equal to or lower than 1.2 with respect to the laser beam having the wavelength of 390 to 420 nm and has a property of absorbing the laser beam having the wavelength of 390 to 420 nm to be melted or decomposed, whereby the refractive index thereof changes.

In a preferred aspect of the present invention, each R in the general formula (1) is independently selected from the group consisting of

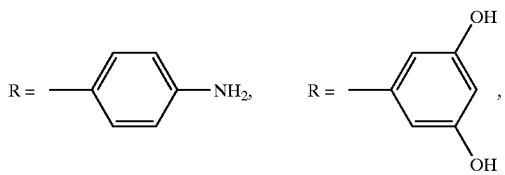

-continued

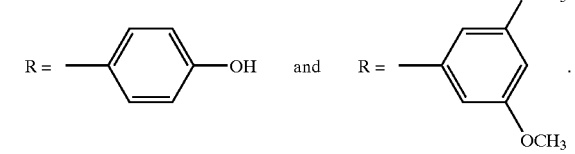

In a preferred aspect of the present invention, the recording layer further contains a ketone system solvent whose carbon number is 5 to 7.

In a further preferred aspect of the present invention, the recording layer further contains a ketone system solvent whose carbon number is 6.

In the present invention, the ketone system solvent may have a chain structure or a ring-shaped structure but a ketone system solvent having a linear chain structure and a branch structure is preferable.

In a preferred aspect of the present invention, the support substrate is formed of a polyolefin resin.

According to this preferred aspect of the present invention, since the support substrate is formed of a polyolefin resin, it is possible to reliably prevent the support substrate from being damaged by a ketone system solvent whose carbon number is 5 to 7.

In a preferred aspect of the present invention, the support substrate is formed of an amorphous polyolefin resin.

In a preferred aspect of the present invention, the optical recording disk further includes a thin film formed of a metal and/or a dielectric material on the support substrate.

In the present invention, the thin film formed of a metal and/or a dielectric material has a thickness of 5 to 70 nm and preferably has a thickness of 10 to 40 nm. Illustrative examples of metals for forming the thin film include Ag and alloy containing Ag as a primary component and illustrative examples of dielectric materials include $Al_2O_3$ and ZnS+$SiO_2$ (mole ratio of 80:20). It is possible to suppress heat influence between neighboring record marks and adjust the reflective coefficient of the optical recording disk by providing such a thin film.

In a preferred aspect of the present invention, the optical recording disk further includes a dielectric film whose refractive index (real part of complex refractive index) n is equal to or higher than 1.8 on the support substrate.

In the present invention, the dielectric film has a thickness of 5 to 100 nm and preferably has a thickness of 20 to 70 nm. When the thickness of the dielectric film exceeds 100 nm, the sensitivity of the optical recording disk is undesirably lowered. Illustrative examples of dielectric materials used to form the dielectric film include $CeO_2+Al_2O_3$ (mole ratio of 80:20), ZnS+$SiO_2$ (mole ratio of 80:20) and the like.

In a preferred aspect of the present invention, the recording layer further contains a quencher.

The above and other objects and features of the present invention will become apparent from the following description made with reference to the accompanying drawing.

BRIEF DESCRIPTION OF THE DRAWING

A preferred but exemplary embodiment of the invention will now be described with reference to the accompanying FIGURE which is an enlarged schematic cross-sectional view showing the substantial part of an optical recording disk.

DESCRIPTION OF THE PREFERRED EMBODIMENTS

The accompanying FIGURE is an enlarged schematic cross-sectional view showing the substantial part of an optical recording disk that is a preferred embodiment of the present invention.

As shown in the FIGURE, an optical recording disk 1 according to this embodiment includes a support substrate 2 and on the surface of the support substrate 2 on which a small concavo-convex pattern constituted by information pits, pre-grooves and the like is formed, a metal layer 3, a dielectric layer 4, a recording layer 5, a dielectric layer 6 and a light transmission layer 7 are formed in this order.

The optical recording disk 1 is constituted so that a laser beam for recording or reproducing data is projected in a direction indicated by an arrow in the FIGURE onto the recording layer 5 via the light transmission layer 7.

The support substrate 2 has a thickness of 0.3 mm to 1.6 mm, preferably, 0.5 mm to 1.3 mm and is formed with a small concavo-convex pattern constituted by information pits, pre-grooves, lands and the like on the surface thereof on which the recording layer 5 is to be formed. In this specification, grooves G mean guide grooves formed on the incidence side of the laser beam and lands L are formed between neighboring grooves. The grooves G are normally formed spirally.

The depth Gd of the groove G is defined as the difference between the highest portion of the land L and the lowest portion of the groove G and is preferably 40 to 150 nm, more preferably, 60 to 120 nm. It is possible to control tracking in a desired manner and suppress crosstalk by setting the depth Gd of the groove G within this range. When the depth Gd of the groove G is smaller than 40 nm, a tracking error signal necessary for following the track becomes low and crosstalk becomes large. Further, a pre-format signal such as a wobble signal tends to become undesirably low. On the other hand, when the depth Gd of the groove G exceeds 150 nm, it becomes difficult to accurately form the groove G and the lands L and there are risks of reduction in a reflective signal and reduction of the sensitivity.

The width Gw of the groove G is defined by a width of the groove G at a position whose depth is a half of the depth Gd of the groove G and is preferably 110 to 210 nm, more preferably, 130 to 190 nm. The pitch Gp of the grooves G is defined by the interval between neighboring grooves G and defined by the distance between the centers of neighboring grooves G in the direction of groove width Gw, for example. The pitch Gp of the grooves G is 290 to 350 nm, for example, and preferably 310 to 330 nm. Crosstalk can be suppressed by setting the groove pitch Gp in this manner.

In this embodiment, data may be recorded on portions of the lands L and the groves G, or portions of the lands L or portions of the grooves G of the optical recording disk 1.

It is not absolutely necessary for the support substrate 2 to be optically transparent but it is preferable for a material insoluble into a solvent used for forming the recording layer 5 to be used for forming the support substrate 2. From this viewpoint, plastic materials such as an acrylic resin like polymethyl methacrylate, a polyolefin resin or the like can be used for forming the support substrate 2. Among these, a polyolefin resin is particularly preferable from the viewpoints of easy processing and the like. For preventing the support substrate 2 from warping, it is particularly advantageous to form the support substrate 2 of a flexible material such as a plastic material. Nevertheless, the support substrate 2 may be formed of glass, ceramic, metal or the like. In the case where the support substrate 2 is formed of a plastic material, the concavo-convex pattern of the surface of the support substrate 2 is often formed when the support substrate 2 is formed using an injection molding process. In the case where the support substrate 2 is formed of a material other than a plastic material, the concavo-convex pattern of the surface of the support substrate 2 may be formed using a photopolymer process (2P process).

In this embodiment, the metal layer 3 and the dielectric layer 4 are formed on the support substrate 2. The metal layer 3 and the dielectric layer 4 serve to effectively radiate heat generated when data are recorded by the laser beam. The metal layer 3 can be formed of, for example, Mg, Al, Ti, Cr, Fe, Co, Ni, Cu, Zn, Ge, Ag, Pt, Au, Nd, Sn, Pd or alloy of these elements. The dielectric layer 4 can be formed of, for example, oxide, nitride, sulfide, fluoride or a combination thereof containing at least one metal selected from the group consisting of Si, Zn, Al, Ta, Ti, Co, Zr, Pb, Ag, Sn, Ca, Ce, V, Cu, Fe, Mg. It is particularly preferable to form the dielectric layer 4 of ZnS—SiO$_2$, Al$_2$O$_3$ or the like. In the case where the dielectric layer 4 is formed of ZnS—SiO$_2$, it is preferable to set the content of SiO$_2$ to be equal to or more than 10 mol % and less than 40 mol %. Illustrative examples of processes for forming the metal layer 3 and the dielectric layer 4 include the ion beam sputtering process, reactive sputtering process, RF sputtering process and the like.

The thicknesses of the metal layer 3 and the dielectric layer 4 are not particularly limited and are, for example, about 5 to 50 nm, preferably, about 5 to 30 nm. When the metal layer 3 and the dielectric layer 4 are thinner than 5 nm, heat cannot be radiated in a desired manner. On the other hand, when the thicknesses of the metal layer 3 and the dielectric layer 4 exceed 50 nm, the heat conductance thereof becomes too high and there is a risk of reducing the sensitivity.

The recording layer 5 containing an organic compound as a primary component is then formed. The organic compound contains a porphyrin system dye represented by general formula (1) as a primary component.

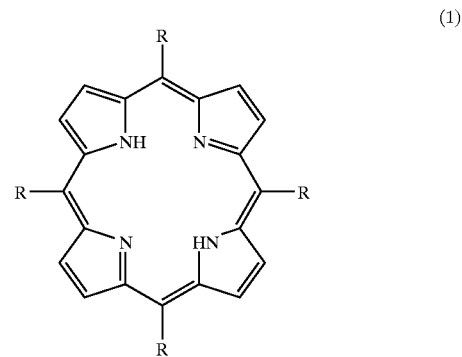

(1)

The case where the recording layer contains an organic compound as a primary component as termed herein includes the case where the recording layer is formed solely of an organic compound and unavoidable components, the case where the recording layer contains organic compounds other than the porphyrin system dye and the case where the recording layer is added with an organic compound in an amount equal to or more than 10 weight % in order to improve characteristics of the recording layer.

It is preferable for the porphyrin system dye to have a minimal value n$_{min}$ of a refractive index (real part of complex refractive index) n within a wavelength range from 370 nm to 425 nm and a refractive index n equal to or lower than 1.2 with respect to the laser beam having the wavelength of 390 to 420 nm and have a property of absorbing the laser beam having the wavelength of 390 to 420 nm for recording data to be melted or decomposed, whereby the refractive index thereof changes.

In the case of using the porphyrin system dye having a refractive index n equal to or lower than 1.2 with respect to the laser beam having the wavelength of 390 to 420 nm for recording data, when data are to be recorded in the recording layer, the porphyrin system dye absorbs the laser beam having the wavelength of 390 to 420 nm for recording data to be melted or decomposed, whereby the refractive index n with respect to the laser beam of a wavelength of 390 to 420 nm changes from a low value to a high value of, for example, 1.45 to 1.65. Thus, a record pit is formed and data are recorded. When data are to be reproduced, data are read utilizing the difference in the reflection coefficients with respect to the laser beam of a wavelength of 390 to 420 nm for reproducing data between the record pit and unrecorded regions around the record pit. Based on these principles, data are recorded using the laser beam of a wavelength of 390 to 420 nm for recording data and data are reproduced using the laser beam of a wavelength of 390 to 420 nm for reproducing data. In order to greatly change the refractive coefficient, the minimal value $n_{min}$ of the refractive index n within a wavelength range from 370 to 425 nm is preferably equal to or lower than 1.1, more preferably, 1.0. The lower limit of the minimal value $n_{min}$ of the refractive index n is not particularly limited but is normally about 0.7.

Further, the extinction coefficient (imaginary part of the complex refractive index) k of the porphyrin system dye is preferably equal to or higher than 0.15 with respect to the laser beam for recording data and the laser beam for reproducing data and more preferably equal to or higher than 0.3. In the case where the extinction coefficient k of the porphyrin system dye with respect to the laser beam for recording data is equal to or higher than 0.15, the laser beam for recording data can be suitably absorbed by the porphyrin system dye at a position where a record pit is to be formed, whereby the temperature is increased locally and the refractive index readily changes due to melting or decomposition of the porphyrin system dye. On the other hand, in the case where the extinction coefficient k of the porphyrin system dye with respect to the laser beam for recording data is lower than 0.15, the absorption of the laser beam for recording data is reduced and it is difficult to record data using a laser beam of ordinary recording power. Further, in the case where the extinction coefficient k of the porphyrin system dye with respect to the laser beam for reproducing data is equal to or higher than 0.15, the unrecorded regions have desired reflection coefficients and it is easy to read the difference in reflection coefficients between the record pit and unrecorded regions. However, the extinction coefficient k of the porphyrin system dye with respect to the laser beam for reproducing data is preferably equal to or lower than 2.0 because the reflective coefficient decreases if the extinction coefficient k of the porphyrin system dye with respect to the laser beam for reproducing data becomes too high. From these viewpoints, the extinction coefficient (imaginary part of the complex refractive index) k of the porphyrin system dye is preferably equal to or higher than 0.3 and equal to or lower than 2.0 with respect to the laser beam for recording data and the laser beam for reproducing data and more preferably equal to or higher than 0.4 and equal to or lower than 1.5.

The refractive index (real part of complex refractive index) n and the extinction coefficient (imaginary part of the complex refractive index) k of the porphyrin system dye are measured by measuring the absorption spectrum of a thin film of the porphyrin system dye. The absorption spectrum of a thin film of the porphyrin system dye is generally measured in the following manner: the organic compound whose absorption spectrum is to be measured is dissolved into a suitable organic solvent to prepare a solution and the thus prepared solution is applied onto a flat polycarbonate plate having no groove or pit using a spin coating process to form a thin film having a thickness of about 40 to 100 nm in such a manner that the organic compound does not have a particular orientation. If the organic compound is markedly crystallized or associated when the solvent is volatized after the spin coating of the solution, another kind of solvent should be selected. The transmittance spectrum and absorption spectrum of the polycarbonate plate formed with the thin film of the organic compound is measured using a spectrophotometer.

In the present invention, it is preferable to independently select each R in the general formula (1) of the porphyrin system dye from the group consisting of

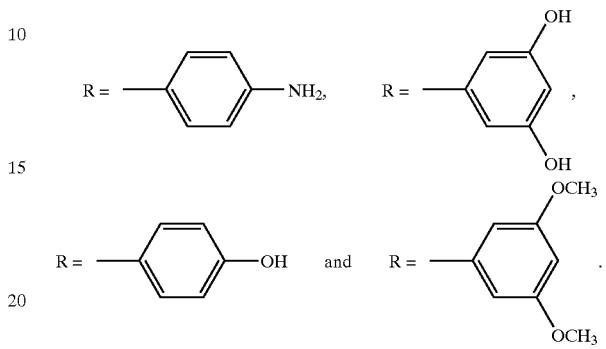

The recording layer 5 is preferably formed using a spin coating process. More specifically, the porphyrin system dye is dissolved into a ketone system solvent to prepare a coating solution and the thus prepared coating solution is applied onto the support substrate 2 using the spin coating process. The coated layer is then dried as occasion demands. The recording layer 5 may be formed using a screen printing process, a dip coating process or the like instead of the spin coating process.

As the solvent for dissolving the porphyrin system dye, it is preferable to employ a ketone system solvent whose carbon number is 5 to 7 and it is more preferable to employ a ketone system solvent having a linear chain structure and a branch structure. Illustrative examples of a ketone system solvent whose carbon number is 5 to 7 and having a linear chain structure and a branch structure include 3-pentanone, methyl isobutyl ketone, 3-hexanone, 2-hexanone(butyl ketone), 4-heptanone, and 2-heptanone.

It is more preferable to employ as the ketone system solvent for dissolving the porphyrin system dye one whose carbon number is 6, particularly, one whose carbon number is 6 and which has a linear chain structure and a branch structure Illustrative examples of such ketone system solvents include methyl isobutyl ketone, 3-hexanone and 2-hexanone(butyl methyl ketone).

The recording layer 5 is formed so as to have a thickness of 30 to 120 nm at the portions of the lands L, more preferably, 40 to 80 nm. The recording layer 5 is formed to a thickness of 5 to 95 μm, preferably, 10 to 80 nm at the portions of the groove G The thickness of the recording layer 5 is preferably designed with consideration to the desired reflective coefficient, modulation and heat interference between neighboring tracks and marks. Illustrative examples of parameters affecting these factors include the shape of the support substrate 2, the behavior of the dye when being thermally decomposed, the optical properties of the dye, the optical properties and thermal conductivity of neighboring layers and the like.

The dielectric layer 6 is preferably formed on the recording layer 5. The dielectric layer 6 serves to mechanically and chemically protect the recording layer 5 and serves as an interference layer for adjusting the optical properties of the recording layer 5. The dielectric layer 5 may have a single-layer structure or a multi-layered structure.

Since the dielectric layer 6 is located on the recording layer 5, it is indispensable for the dielectric layer 6 to have a property of transmitting the laser beam of a wavelength of 390 to 420 nm for recording data and the laser beam of a wavelength of 390 to 420 nm for reproducing data and it is preferable for the dielectric layer 6 to have a refractive index (real part of at the complex refractive index) $n_4$ equal to or higher than 2 with respect to the laser beam of a wavelength of 390 to 420 nm for recording data and the laser beam of a wavelength of 390 to 420 nm for reproducing data. In the case where the refractive index $n_4$ of the dielectric layer 6 is equal to or higher than 2, the reflective coefficient of the optical recording disk 1 can be easily adjusted to within a desired range. The upper limit of the refractive index $n_4$ of the dielectric layer 6 is not particularly limited but the upper limit of the refractive index $n_4$ of materials known to be capable of transmitting light having a wavelength of 390 to 420 nm is ordinarily about 3. On the other hand, it is preferable for the dielectric layer 6 to have an extinction coefficient (imaginary part of the complex refractive index) $k_4$ equal to or lower than 0.2 with respect to the laser beam of a wavelength of 390 to 420 nm for recording data and the laser beam of a wavelength of 390 to 420 nm for reproducing data. In the case where the extinction coefficient $k_4$ of the dielectric layer 6 is equal to or lower than 0.2, the energy of the laser beam absorbed in the dielectric layer 6 is reduced, thereby increasing the margin for adjusting the reflective coefficient of the optical recording disk 1 and enabling improvement of the sensitivity of optical recording disk 1. The lower limit of the extinction coefficient $k_4$ of the dielectric layer 6 is not particularly limited but is about 0.

The dielectric layer 6 can be formed of oxide, nitride, sulfide, fluoride or a combination thereof containing at least one metal selected from the group consisting of Si, Zn, Al, Ta, Ti, Co, Zr, Pb, Ag, Sn, Ca, Ce, V, Cu, Fe and Mg but from the viewpoint of the above described preferable ranges of the refractive index $n_4$ and the extinction coefficient $k_4$ of the dielectric layer 6, the dielectric layer 6 is preferably formed of $ZnS$—$SiO_2$, $AlN$, $Ta_2O_3$, $CeO_2$—$Al_2O_3$ or the like. In order to achieve desired optical properties and physical properties, the content of $SiO_2$ in $ZnS$—$SiO_2$ is preferably equal to or more than 10 mol % and the content of $Al_2O_3$ in $CeO_2$—$Al_2O_3$ is preferably equal to or more than 40 mol %. Illustrative examples of processes for forming the dielectric layer 6 include the ion beam sputtering process, reactive sputtering process, RF sputtering process and the like, and any process which does not damage the recording layer 5 may be suitably selected.

The thickness of the dielectric layer 6 is not particularly limited and is, for example, about 20 to 150 nm, preferably, about 30 to 70 nm. When the dielectric layer 6 is thinner than 20 nm, components of the light transmission layer 7 sometimes permeate the dielectric layer 6, thereby damaging the recording layer 5. On the other hand, when the thickness of the dielectric layer 6 exceeds 150 nm, the thermal conductivity becomes too high and there is a risk of reducing the sensitivity of the optical recording disk 1.

The light transmission layer 7 is formed on the dielectric layer 6.

The material for forming the light transmission layer 7 is not particularly limited insofar as it is optically transparent and the absorption, reflection and birefringence thereof are small with respect to light within the same wavelength region as that of the laser beam having a wavelength of 390 to 420 nm. The material for forming the light transmission layer 7 can be selected from among an ultraviolet ray curable resin, an electron beam curable resin and a thermosetting resin. An ultraviolet ray curable resin or an electron beam curable resin is particularly preferable. The material for forming the light transmission layer 7 is preferably a solvent-free type material.

Preferably, the light transmission layer 7 is formed of a monomer, oligomer or polymer of an ultraviolet ray curable resin or an electron beam curable resin or a mixture thereof which may contain additives such as a polymerization initiator. Illustrative examples of ultraviolet ray curable resins, electron beam curable resins and mixtures thereof for polymerization include a monomer, oligomer and polymer containing or introduced with, in molecules, groups such as acrylic double bonds of ester compounds of acrylic acid, methacrylic acid or the like, epoxy acrylates, urethane acrylates or the like, allylic double bonds of diallyl phthalates or the like, unsaturated double bonds of maleic acid derivatives or the like, each of which is bridgeable or polymerizable by irradiation with an ultraviolet ray or an electron beam. Each is preferably a multifunctional compound, in particular, a compound containing three or more functional groups and may be used alone or in combination with others. Each may contain a monofunctional compound.

A compound having a molecular weight of less than 2,000 is preferable as an ultraviolet ray curable monomer, while an ultraviolet ray curable oligomer preferably has a molecular weight of 2,000 to 10,000. Illustrative examples include styrene, ethyl acrylate, ethylene glycol diacrylate, ethylene glycol dimethacrylate, diethylene glycol diacrylate, diethylene glycol methacrylate, 1,6-hexane glycol diacrylate, 1,6-hexane glycol dimethacrylate and the like. Among these, pentaerythritol tetra(metha)acrylate, pentaerythritol (metha) acrylate, trimethylolpropane tri(metha)acrylate, trimethylolpropane di(metha)acrylate, (metha)acrylate of phenol ethylene oxide adduct and the like are particularly preferable. Illustrative examples of other ultraviolet ray curable oligomers include oligoester acrylate, an acrylic modified compound of urethane elastomer and the like.

As an ultraviolet ray curable material, a compound containing an epoxy resin and a photo cationic polymerization catalyst is preferably used. As an epoxy resin, a cycloaliphatic epoxy resin is preferable and an epoxy resin having two or more epoxy groups in the molecule thereof is particularly preferable. In the case where the ultraviolet ray curable material contains two or more cycloaliphatic epoxy resins, it is preferable for the ultraviolet ray curable material to contain at least one cycloaliphatic epoxy resin selected from the group consisting of 3,4-epoxy cyclohexyl methyl-3,4-epoxy cyclohexane carboxylate, bis-(3,4-epoxy cyclohexyl methyl) adipate, bis-(3,4-epoxy cyclohexyl) adipate, 2-(3,4-epoxy cyclohexyl-5,5-spiro-3,4-epoxy) cyclohexane-metha-dioxane, bis-(2,3-epoxy cyclopentyl) ether and vinyl cyclohexene dioxide. The epoxy equivalent of the cycloaliphatic epoxy resin is not particularly limited but from the viewpoint of excellent curability, the epoxy equivalent thereof is preferably 60 to 300, more preferably 100 to 200.

The photo cationic polymerization catalyst is not particularly limited and known photo cationic polymerization catalysts can be employed. As the photo cationic polymerization catalyst there can be used, for example, a complex of at least one metal fluoroborate and a boron trifluoride, a bis-(perfluoro alkylsulfonyl) methane metal salt, an aryl diazonium compound, an aromatic onium salt of a 6A group element, an aromatic onium salt of a 5A group element, a dicarbonyl chelate of a 3A group element to a 5A group element, a thiopyrylium salt, a 6A group element containing an $MF_6$ anion where M is P, As or Sb), a triaryl sulfonium complex salt, an aromatic iodonium complex salt, an aromatic sulfonium complex salt or the like. It is particularly preferable to employ as the photo cationic polymerization catalyst at least one of a polyaryl sulfonium complex salt, an aromatic sulfonium salt of a complex ion containing halogen, an aromatic iodonium salt of a complex ion containing halogen, an aromatic onium salt of a 3A group element, an aromatic onium salt of a 5A group element and an aromatic onium salt of a 6A group element.

The ultraviolet ray curable resin or the electron beam curable resin for forming the light transmission layer 7 preferably has a viscosity of 1,000 to 10,000 centipoise at 25° C.

The light transmission layer 7 is preferably formed by applying the ultraviolet ray curable resin or the electron beam curable resin on the dielectric layer 6 using a spin coating process to form a coating layer and projecting an ultraviolet ray or an electron beam onto the coating layer, thereby curing it.

Further, the light transmission layer 7 may be formed by bonding a sheet formed to the desired thickness of a resin which is optically transparent and whose absorption, reflection and birefringence are small with respect to light within the same wavelength region as that of the laser beam having a wavelength of 390 to 420 nm onto the dielectric layer 6 using an adhesive agent which is optically transparent and whose absorption, reflection and birefringence are small with respect to light within the same wavelength region as that of the laser beam having a wavelength of 390 to 420 nm.

Illustrative examples of the resins usable for forming the sheet for forming the light transmission layer 7 include polycarbonate, amorphous polyolefin, polyester and the like. Prior to bonding of the resin sheet, an annealing treatment (thermal relaxation treatment) may be effected on the resin sheet in the temperature region of −20 to +80° C. relative to the thermal deformation temperature of the resin, thereby removing residual stress generated in the resin sheet when it was formed. In the case where no annealing treatment is effected on the resin sheet, there is a risk of the optical recording disk 1 being deformed due to residual stress in the sheet during the storage of the optical recording disk 1. The heating means for performing the annealing treatment can be suitably selected based on the annealing treatment conditions from among from known heating means such as a heater, a hot plate, a hot roller, a baking oven, an electromagnetic induction heating means and the like.

The adhesive agent for bonding the resin sheet can be selected from among a pressure sensitive agglutinant, an ultraviolet ray curable resin and the like. For example, the ultraviolet ray curable resin or the electron beam curable resin described as the material for the light transmission layer 7 is suitable for the adhesive agent for bonding the resin sheet.

In the case where the light transmission layer 7 is formed by bonding the resin sheet onto the dielectric layer 6, it is preferable to form the light transmission layer 7 by applying the ultraviolet ray curable resin or the electron beam curable resin as an adhesive agent onto the dielectric layer 6 using a spin coating process to form an ultraviolet ray curable resin layer or an electron beam curable resin layer, placing the resin sheet on the uncured ultraviolet ray curable resin layer or electron beam curable resin layer, and projecting an ultraviolet ray or an electron beam onto the ultraviolet ray curable resin layer or the electron beam curable resin layer to cure the ultraviolet ray curable resin layer or the electron beam curable resin layer and bond the resin sheet on the dielectric layer 6. More specifically, the resin sheet is placed on the uncured ultraviolet ray curable resin layer or electron beam curable resin layer under a vacuum condition, namely, under an ambient pressure equal to or lower than 0.1 atm, the ambient pressure is returned to atmospheric pressure and an ultraviolet ray or electron beam is projected onto the uncured ultraviolet ray curable resin layer or electron beam curable resin layer, thereby curing the ultraviolet ray curable resin layer or the electron beam curable resin layer.

The thickness t of the light transmission layer 7 generally correlates with a disk skew margin θ (hereinafter referred to as skew-margin θ), the wavelength λ of the laser beam for recording and reproducing data and the numerical aperture NA of an objective lens. The relationship between these parameters and the skew margin is expressed as $\theta \propto \lambda/\{t \times (NA)^3\}$ in Japanese Patent Application Laid Open No. 3-225650.

During actual volume production of the optical recording disk 1, if the skew margin θ is set to 0.4° considering yield ratio and cost, and the relationships λ=380 nm and NA>0.76 are established in light of the need to shorten the wavelength of the laser beam and increase the numerical aperture NA of the objective lens, it the becomes possible to ensure substantially the same level of the skew margin θ as that of the DVD by setting the thickness t of the light transmission layer 7 to equal to or thinner than 170 μm.

On the other hand, the lower limit of the thickness of the light transmission layer 7 is preferably equal to or thicker that 1 μm for protecting the dielectric layer 6 and the recording layer 5 in a desired manner. In the case where the light transmission layer 7 is formed using a sheet-like resin, it is difficult to form the light transmission layer 7 so as to be uniform and thin. In such case, therefore, the lower limit of the total thickness of the light transmission layer 7 and the adhesive agent layer is preferably equal to or thicker than 50 μm. Thus in the case where the light transmission layer 7 is formed using a spin coating process, the thickness t thereof is preferably 1 to 150 μm and in the case where the light transmission layer 7 is formed by bonding a sheet-like resin, the thickness t thereof is preferably 50 to 150 μm.

EXAMPLES

Hereinafter, working examples and comparative examples will be set out in order to further clarify the advantages of the present invention.

Working Example 1

The support substrate 2 was prepared to a diameter of 120 mm and a thickness of 1.1 mm from a grooved polyolefin resin substrate formed of "Zeonex" (trade name of a product manufactured by ZEON Corporation), a polyolefin resin containing repeating units represented by the following structural formula obtained by ring-opening polymerizing norbornene monomers and adding hydrogen thereto.

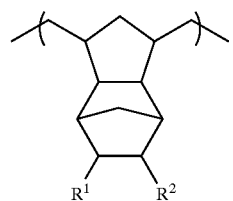

The depth Gd of the grooves G shown in the FIGURE was 85 nm, the width Gw thereof was 160 nm and the pitch (track pitch) Gp of the grooves G was 320 nm.

0.14 grams of a porphyrin system dye represented by the following structural formula (1) was dissolved into 9.86 grams of methyl isobutyl ketone to prepare a coating solution having a porphyrin system dye concentration of 1.4 weight % and the thus prepared coating solution was applied onto the support substrate 2 using a spin coating process to form the recording layer 5 to an average thickness of about 40 nm at the portions of the lands L and the portions of the grooves G.

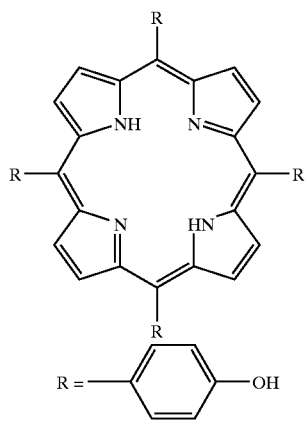

(1)

The absorption spectrum of a thin film of this porphyrin system dye had a minimal value $n_{min}$ of a refractive index (real part of complex refractive index) n at the wavelength of 399 nm. The minimal value $n_{min}$ was 0.79. The refractive index n of this porphyrin system dye at the wavelength of 405 nm was 0.8 and the extinction coefficient (imaginary part of the complex refractive index) k of this porphyrin system dye was 0.87.

The dielectric layer 6 was formed by using the RF sputtering process to form an approximately 50 nm thick layer of ZnS (80 mol %)-$SiO_2$ (20 mol %) on the recording layer 5 formed to an average thickness of about 40 nm. The refractive index (real part of complex refractive index) $n_4$ of the dielectric layer 6 was 2.3 and the extinction coefficient (imaginary part of the complex refractive index) $k_4$ thereof was 0.

An ultraviolet ray curable resin having a viscosity of 5,000 centipoise at 25° C. was applied onto the dielectric layer 6 using the spin coating process to form a coating layer and ultraviolet rays were projected onto the thus formed coating layer, thereby curing the ultraviolet ray curable resin and forming a light transmission layer 7 having a thickness of about 100 µm.

Thus, an optical recording disk sample #1 was fabricated.

Working Example 2

An optical recording disk sample #2 was fabricated in the manner of Working Example 1 except that 0.13 grams of the porphyrin system dye used in Working Example 1 was dissolved into 9.87 grams of 3-pentanon to prepare a coating solution having a porphyrin system dye concentration of 1.3 weight %.

Working Example 3

An optical recording disk sample #3 was fabricated in the manner of Working Example 1 except that 0.15 grams of the porphyrin system dye used in Working Example 1 was dissolved into 9.85 grams of 2-hexanon to prepare a coating solution having a porphyrin system dye concentration of 1.5 weight %.

Working Example 4

An optical recording disk sample #4 was fabricated in the manner of Working Example 1 except that 0.15 grams of the porphyrin system dye used in Working Example 1 was dissolved into 9.85 grams of 3-hexanon to prepare a coating solution having a porphyrin system dye concentration of 1.5 weight %.

Working Example 5

An optical recording disk sample #5 was fabricated in the manner of Working Example 1 except that a dielectric layer having a thickness of about 30 nm was formed.

Working Example 6

An optical recording disk sample #6 was fabricated in the manner of Working Example 1 except that the dielectric layer 6 consisted of a layer of $CeO_2$ (80 mol %)-$AL_2O_3$ (20 mol %) having a thickness of about 40 nm that was formed on the recording layer 5 using the RF sputtering process.

Working Example 7

An optical recording disk sample #7 was fabricated in the manner of Working Example 1 except that a dielectric layer 4 consisting of ZnS (80 mol %)-$SiO_2$ (20 mol %) and having a thickness of about 10 nm was formed on the support substrate 2 using an RF sputtering process and the recording layer was formed on the dielectric layer 4.

Working Example 8

An optical recording disk sample #8 was fabricated in the manner of Working Example 1 except that a metal layer 3 consisting of AgNdCu alloy and having a thickness of about 10 nm was formed on the support substrate 2 using the RF sputtering process and the recording layer was formed on the metal layer 3.

Working Example 9

An optical recording disk sample #9 was fabricated in the manner of Working Example 1 except that a metal layer consisting of AgNdCu alloy and having a thickness of about 20 nm was formed on the support substrate 2 using the RF sputtering process and the recording layer was formed on the metal layer 3.

Working Example 10

An optical recording disk sample #10 was fabricated in the manner of Working Example 1 except that a dielectric layer 4 consisting of $Al_2O_3$ and having a thickness of about 10 nm was formed on the support substrate 2 using the RF sputtering process and the recording layer was formed on the dielectric layer 4.

Working Example 11

0.14 grams of a porphyrin system dye represented by the following structural formula (1) was dissolved into 9.86 grams of methyl isobutyl ketone to prepare a coating solution having a porphyrin system dye concentration of 1.4 weight % and the thus prepared coating solution was applied onto the support substrate 2 using a spin coating process to form a recording layer 5 having an average thickness of about 40 nm at the portions of the lands L and the portions of the grooves G.

19

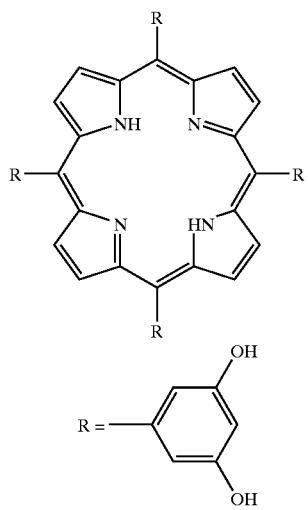

(1)

The absorption spectrum of a thin film of this porphyrin system dye had a minimal value $n_{min}$ of a refractive index (real part of complex refractive index) n at the wavelength of 406 nm. The minimal value $n_{min}$ was 1.00. The refractive index n of this porphyrin system dye at the wavelength of 405 nm was 1.0 and the extinction coefficient (imaginary part of the complex refractive index) k of this porphyrin system dye was 0.86.

A dielectric layer 6 and a light transmission layer 7 were formed on the thus formed recording layer in the manner of Working Example 1, thereby fabricating an optical recording disk sample #11.

Working Example 12

0.13 grams of a porphyrin system dye represented by the following structural formula (1) was dissolved into 9.86 grams of methyl isobutyl ketone to prepare a coating solution having a porphyrin system dye concentration of 1.3 weight % and the thus prepared coating solution was applied onto the support substrate 2 using a spin coating process to form a recording layer 5 having an average thickness of about 30 nm at the portions of the lands L and the portions of the grooves G.

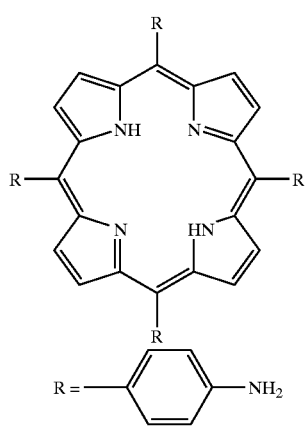

(1)

The absorption spectrum of a thin film of this porphyrin system dye had a minimal value $n_{min}$ of a refractive index (real part of complex refractive index) n at the wavelength of 416 nm. The minimal value $n_{min}$ was 1.06. The refractive index n of this porphyrin system dye at the wavelength of 405 nm was 1.10 and the extinction coefficient (imaginary part of the complex refractive index) k of this porphyrin system dye was 0.34.

A dielectric layer 6 and a light transmission layer 7 were formed on the thus formed recording layer in the manner of Working Example 1, thereby fabricating an optical recording disk sample #12.

Comparative Example 1

0.8 grams of an organic dye represented by the following structural formula was dissolved into 9.92 grams of tetrafluoropropanol to prepare a coating solution having an organic dye concentration of 0.8 weight % and the thus prepared coating solution was applied onto the support substrate 2 using a spin coating process to form a recording layer 5 having an average thickness of about 40 nm at the portions of the lands L and the portions of the grooves G.

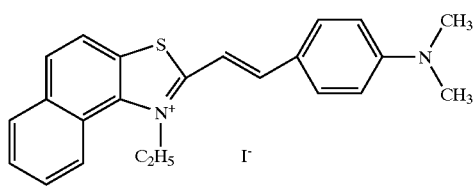

The absorption spectrum of a thin film of this organic dye had a minimal value $n_{min}$ of a refractive index (real part of complex refractive index) n at the wavelength of 432 nm. The minimal value $n_{min}$ was 0.94. The refractive index n of this porphyrin system dye at the wavelength of 405 nm was 1.29 and the extinction coefficient (imaginary part of the complex refractive index) k thereof was 0.25.

A dielectric layer 6 and a light transmission layer 7 were formed on the thus formed recording layer in the manner of Working Example 1, thereby fabricating an optical recording disk comparative sample #1.

Comparative Example 2

0.8 grams of an organic dye represented by the following structural formula was dissolved into 9.92 grams of tetrafluoropropanol to prepare a coating solution having an organic dye concentration of 0.8 weight % and the thus prepared coating solution was applied onto the support substrate 2 using a spin coating process to form a recording layer 5 having an average thickness of about 40 nm at the portions of the lands L and the portions of the grooves G.

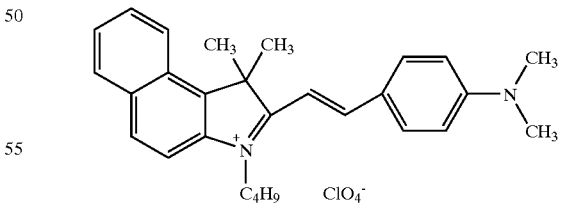

The absorption spectrum of a thin film of this organic dye had a minimal value $n_{min}$ of a refractive index (real part of complex refractive index) n at the wavelength of 472 nm. The minimal value $n_{min}$ was 1.01. The refractive index n of this porphyrin system dye at the wavelength of 405 nm was 1.36 and the extinction coefficient (imaginary part of the complex refractive index) k thereof was 0.03.

A dielectric layer 6 and a light transmission layer 7 were formed on the thus formed recording layer in the manner of Working Example 1, thereby fabricating an optical recording disk comparative sample #2.

Data were recorded in the optical recording disk sample #1 fabricated in Working Example 1 and data were reproduced therefrom in the following manner.

The optical recording disk sample #1 was set in a DDU1000 optical recording medium evaluation apparatus manufactured by Pulstec Industrial Co., Ltd. and a blue laser beam having a wavelength of 405 nm was condensed onto the portions of the lands L of the recording layer 5 via the light transmission layer 7 using an objective lens whose numerical aperture NA was 0.85, thereby recording data and reproducing data.

An 8T signal in accordance with the) RLL (1,7) Modulation Code was used as a recording signal and data were recorded only in one track. A multi-pulse train pattern was used for modulating the power of the laser beam when data were recorded and the multi-pulse train pattern was set so that the length of the foremost pulse was 1T where T was the clock cycle, the length of the last pulse was 1T, the length of each of the multi-pulses between the foremost pulse and the last pulse was 0.4T, the recording power of the laser beam was 10 mW, the length of the shortest pit was 0.16 $\mu$m, and the linear recording density was 0.12 $\mu$M/bit where 0.12 $\mu$m was the channel pit length.

When the thus recorded data were reproduced by ea laser beam whose reproduction power was set at 0.4 mW, a C/N ratio of 53 dB was obtained and excellent signal characteristics could be obtained.

Similar data recording and reproducing tests were effected on the optical recording disk samples #2 to #12. The, C/N ratios obtained therefrom were 52 dB, 51 dB, 51 dB, 52 dB, 50 dB, 54 dB, 56 dB, 55 dB, 55 dB, 53 dB and 48 dB, respectively, and excellent signal characteristics could be obtained.

The data recording and reproducing tests were also similarly effected on the optical recording disk comparative samples #1 and #2. However, the C/N ratios obtained therefrom were 35 dB and 25 dB, respectively. Moreover, the modulation thereof after data recording was small and desired C/N ratios could not be obtained.

The present invention has thus been shown and described with reference to specific embodiments and working examples. However, it should be noted that the present invention is in no way limited to the details of the described arrangements but changes and modifications may be made without departing from the scope of the appended claims.

For example, in the above described embodiment, although the optical recording disk 1 includes the metal layer 3 and the dielectric layer 4 formed on the support substrate 2, it is not absolutely necessary for the optical recording disk 1 to include the metal layer 3 and the dielectric layer 4 formed on the support substrate 2 and one of the metal layer 3 and the dielectric layer 4 may be formed on the support substrate 2 and the recording layer 5 may be directly formed on the support substrate 2 without forming a metal layer 3 and a dielectric layer 4.

Further, in the above described embodiment, although the optical recording disk 1 includes the dielectric layer 6 on the recording layer 5, it is not absolutely necessary for the optical recording disk 1 to include the dielectric layer 6 on the recording layer 5 and the dielectric layer 6 can be omitted.

Furthermore, in the above described working examples, there was used a support substrate formed of "Zeonex" (trade name of a product manufactured by ZEON Corporation), which is a polyolefin resin containing repeating units represented by the following structural formula obtained by ring-opening polymerizing norbornene monomers and adding hydrogen thereto.

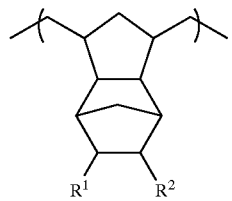

However, the polyolefin resin forming the support substrate 2 is not particularly limited and a support substrate formed of other polyolefin resin can be used. For example, it is possible to employ a support substrate formed of "Arton" (trade name of a product manufactured by JSR Corporation), which is a polyolefin resin containing repeating units represented by the following structural formula.

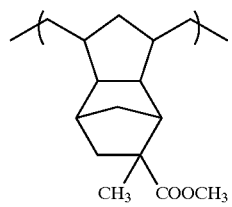

According to the present invention, it is possible to provide an optical recording disk which includes a recording layer containing an organic compound as a primary component, in which data can be recorded using a bluish-violet laser beam having a wavelength of 390 to 420 nm and from which data can be reproduced using a bluish-violet laser beam having a wavelength of 390 to 420 nm.

Further, according to the present invention, it is possible to provide a method for manufacturing an optical recording disk which includes a recording layer containing an organic compound as a primary component, in which data can be recorded using a bluish-violet laser beam having a wavelength of 390 to 420 nm and from which data can be reproduced using a bluish-violet laser beam having a wavelength of 390 to 420 nm.

Furthermore, according to the present invention, it is possible to provide an optical recording and reproducing method capable of recording data in and reproducing from an optical recording disk including a recording layer containing an organic compound as a primary component using a bluish-violet laser beam having a wavelength of 390 to 420 nm.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An optical recording disk comprising a recording layer containing an organic compound as a primary component, the organic compound containing a porphyrin system dye represented by general formula (1) as a primary component.

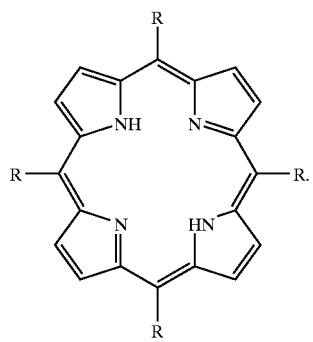

(1)

2. The optical recording disk in accordance with claim 1 which comprises at least a recording layer containing the organic compound containing the porphyrin system dye as a primary component and a light transmission layer which transmits a laser beam having a wavelength of 390 to 420 nm on a support substrate in this order, the porphyrin system dye having a minimal value $n_{min}$ of a refractive index (real part of complex refractive index) n within a wavelength region of 390 nm to 420 nm and a refractive index n equal to or lower than 1.2 with respect to the laser beam having the wavelength of 390 to 420 nm and absorbing the laser beam having the wavelength of 390 to 420 nm to be melted or decomposed, whereby the refractive index thereof changes and data are recorded in the optical recording disk.

3. The optical recording disk in accordance with claim 1, wherein the porphyrin system dye is melted or decomposed by the laser beam, whereby the refractive index n thereof increases.

4. The optical recording disk in accordance with claim 2, wherein the porphyrin system dye is melted or decomposed by the laser beam, whereby the refractive index n thereof increases.

5. The optical recording disk in accordance with claim 1, wherein an extinction coefficient (imaginary part of the complex refractive index) k of the porphyrin system dye is equal to or higher than 1.5 at wavelengths of a laser beam for reproducing data and a laser bream for recording data.

6. The optical recording disk in accordance with claim 2, wherein an extinction coefficient (imaginary part of the complex refractive index) k of the porphyrin system dye is equal to or higher than 1.5 at wavelengths of a laser beam for reproducing data and a laser bream for recording data.

7. The optical recording disk in accordance with claim 1, wherein R in the general formula (1), at each occurrence, is independently selected from the group consisting of

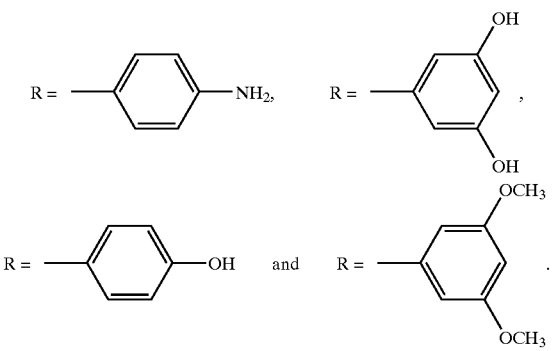

8. The optical recording disk in accordance with claim 2, wherein R in the general formula (1), at each occurrence, is independently selected from the group consisting of

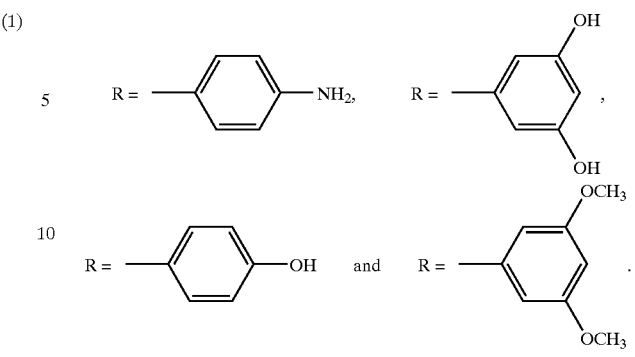

9. The optical recording disk in accordance with claim 1, wherein the recording layer further contains a ketone system solvent whose carbon number is 5 to 7.

10. The optical recording disk in accordance with claim 2, wherein the recording layer further contains a ketone system solvent whose carbon number is 5 to 7.

11. The optical recording disk in accordance with claim 9, wherein the recording layer contains a ketone system solvent whose carbon number is 6.

12. The optical recording disk in accordance with claim 10, wherein the recording layer contains a ketone system solvent whose carbon number is 6.

13. The optical recording disk in accordance with claim 2, wherein the support substrate is formed of a polyolefin resin.

14. The optical recording disk in accordance with claim 2 which further includes a thin film formed of a metal and/or a dielectric material on the support substrate.

15. The optical recording disk in accordance with claim 2 which further includes a dielectric film whose refractive index (real part of complex refractive index) n equal to or higher than 1.8 on the support substrate.

16. The optical recording disk in accordance with claim 1, wherein the recording layer further contains a quencher.

17. The optical recording disk in accordance with claim 2, wherein the recording layer further contains a quencher.

18. A method for manufacturing an optical recording disk comprising steps of dissolving a porphyrin system dye represented by general formula (1) into a ketone whose carbon number is 5 to 7 to prepare a coating solution, and applying the thus prepared coating solution onto a support substrate using a spin coating process to form a recording layer.

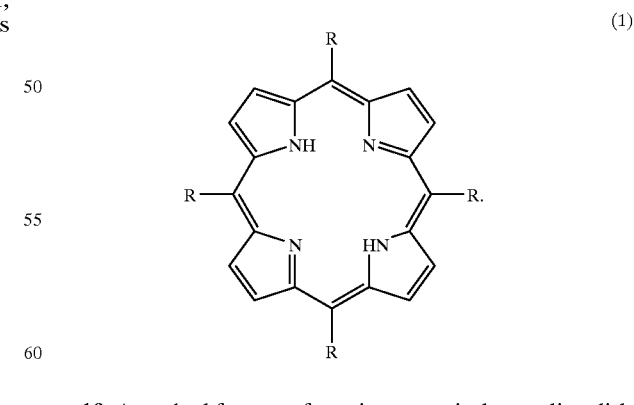

(1)

19. A method for manufacturing an optical recording disk in accordance with claim 18 which comprises steps of dissolving the porphyrin system dye having a minimal value $n_{min}$ of a refractive index (real part of complex refractive index) n within a wavelength region of 390 nm to 420 nm and a refractive index n equal to or lower than 1.2 with respect to the laser beam having the wavelength of 390 to 420 nm into a ketone system solvent whose carbon number is 5 to 7, thereby preparing a coating solution, and applying the thus prepared coating solution onto the support substrate using a spin coating process to form a recording layer.

20. A method for manufacturing an optical recording disk in accordance with claim 18, wherein R in the general formula (1), at each occurrence, is independently selected from the group consisting of

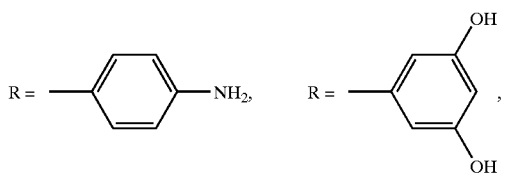

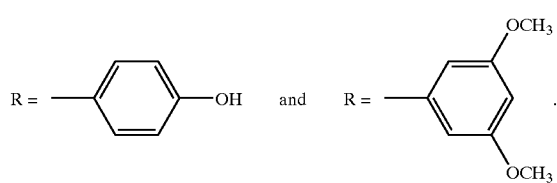

21. A method for manufacturing an optical recording disk in accordance with claim 19, wherein R in the general formula (1), at each occurrence, is independently selected from the group consisting of

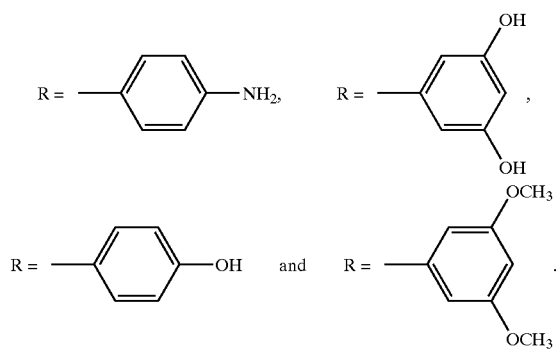

22. A method for manufacturing an optical recording disk in accordance with claim 18, wherein the coating solution is prepared by dissolving the above identified porphyrin system dye into a ketone system solvent whose carbon number is 6.

23. A method for manufacturing an optical recording disk in accordance with claim 19, wherein the coating solution is prepared by dissolving the above identified porphyrin system dye into a ketone system solvent whose carbon number is 6.

24. A method for manufacturing an optical recording disk in accordance with claim 18, wherein the recording layer is formed by applying the coating solution onto the support substrate formed of a polyolefin resin using a spin coating process.

25. A method for manufacturing an optical recording disk in accordance with claim 19, wherein the recording layer is formed by applying the coating solution onto the support substrate formed of a polyolefin resin using a spin coating process.

26. A method for recording and reproducing an optical recording disk including at least a recording layer containing an organic compound as a primary component and a light transmission layer which transmits a laser beam having a wavelength of 390 to 420 nm on a support substrate in this order, the organic compound containing a porphyrin system dye represented by general formula (1) as a primary component, the optical recording and reproducing method comprising steps of projecting a laser beam of a wavelength of 390 to 420 nm for recording data onto the recording layer via the light transmission layer, thereby recording data in the recording layer and increasing a refractive index n of the porphyrin system dye with respect to a laser beam of a wavelength of 390 to 420 nm for reproducing data, and projecting the laser beam of a wavelength of 390 to 420 nm for reproducing data onto the recording layer via the light transmission layer, thereby reproducing data recorded in the recording layer.

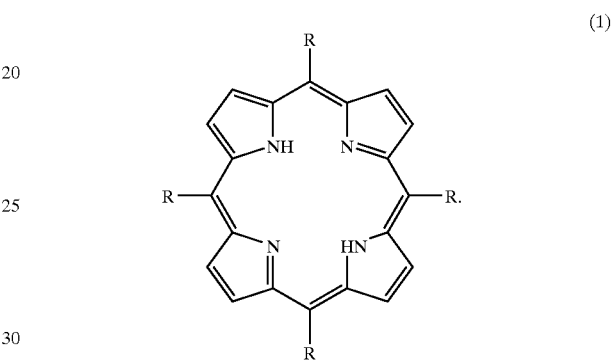

(1)

27. The optical recording and reproducing method for an optical recording disk in accordance with claim 26, wherein the porphyrin system dye has a minimal value $n_{min}$ of a refractive index (real part of complex refractive index) n within a wavelength region of 390 nm to 420 nm and a refractive index n equal to or lower than 1.2 with respect to the laser beam having the wavelength of 390 to 420 nm and has a property of absorbing the laser beam having the wavelength of 390 to 420 nm to be melted or decomposed, whereby the refractive index thereof changes.

28. The optical recording and reproducing method for an optical recording disk in accordance with claim 26, wherein R in the general formula (1), at each occurrence, is independently selected from the group consisting of

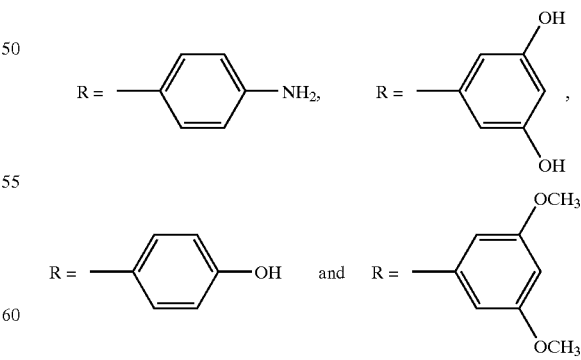

29. The optical recording and reproducing method for an optical recording disk in accordance with claim 27, wherein R in the general formula (1), at each occurrence, is independently selected from the group consisting of 30. The optical recording and reproducing method for an optical recording disk in accordance with claim 26, wherein the recording layer further contains a ketone system solvent whose carbon number is 5 to 7.

31. The optical recording and reproducing method for an optical recording disk in accordance with claim 27, wherein the recording layer further contains a ketone system solvent whose carbon number is 5 to 7.

32. The optical recording and reproducing method for an optical recording disk in accordance with claim 30, wherein the recording layer further contains a ketone system solvent whose carbon number is 6.

33. The optical recording and reproducing method for an optical recording disk in accordance with claim 31, wherein the recording layer further contains a ketone system solvent whose carbon number is 6.

34. The optical recording and reproducing method for an optical recording disk in accordance with claim 26, wherein the support substrate is formed of a polyolefin resin.

35. The optical recording and reproducing method for an optical recording disk in accordance with claim 27, wherein the support substrate is formed of a polyolefin resin.

36. An optical recording disk comprising a recording layer containing an organic compound as a primary component, the organic compound containing a porphyrin system dye represented by general formula (1) as a primary component,

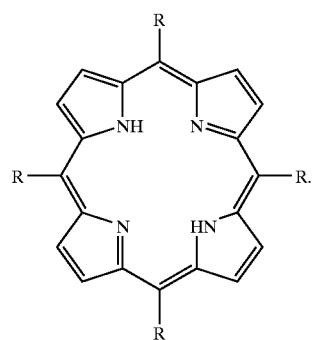

(1)

wherein R in the general formula (1), at each occurrence, is independently selected from the group consisting of

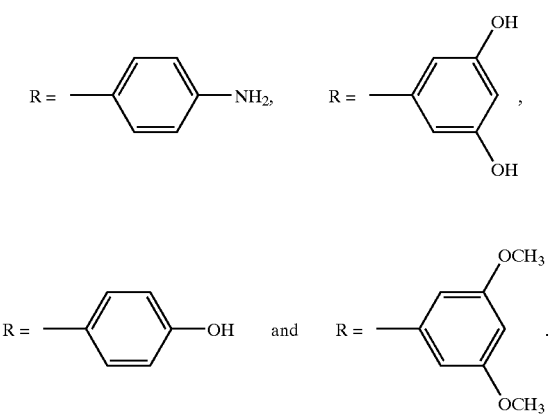

37. The optical recording disk of claim 36 wherein each R of the porphyrin system dye is the same.

38. A method for manufacturing an optical recording disk comprising steps of dissolving a porphyrin system dye represented by general formula (1) into a ketone whose carbon number is 5 to 7 to prepare a coating solution, and applying the thus prepared coating solution onto a support substrate using a spin coating process to form a recording layer,

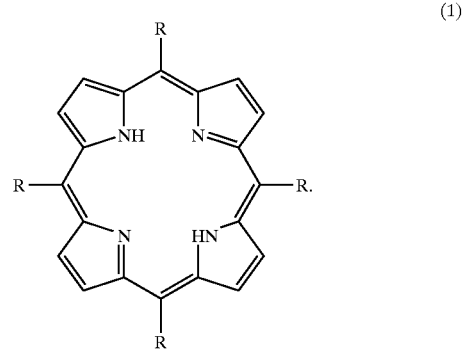

(1)

wherein R in the general formula (1), at each occurrence, is independently selected from the group consisting of

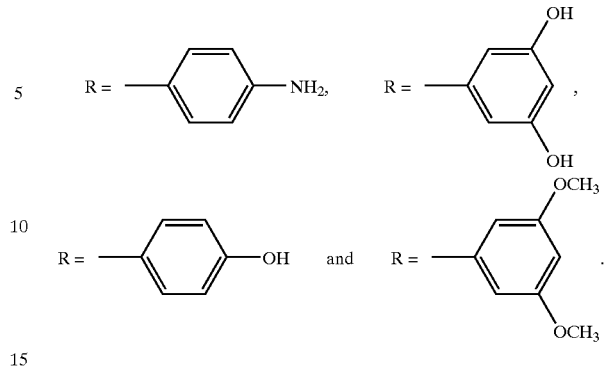

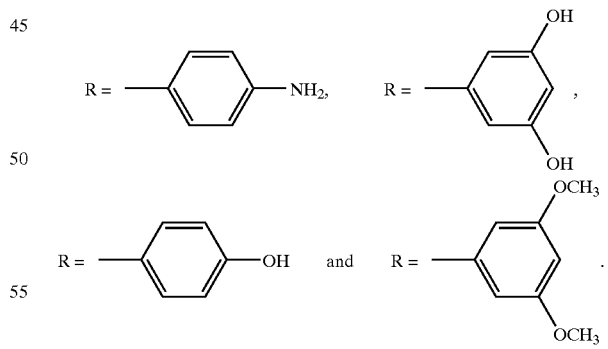

39. A method for recording and reproducing an optical recording disk including at least a recording layer containing an organic compound as a primary component and a light transmission layer which transmits a laser beam having a wavelength of 390 to 420 nm on a support substrate in this order, the organic compound containing a porphyrin system dye represented by general formula (1) as a primary component, the optical recording and reproducing method comprising steps of projecting a laser beam of a wavelength of 390 to 420 nm for recording data onto the recording layer via the light transmission layer, thereby recording data in the recording layer and increasing a refractive index n of the porphyrin system dye with respect to a laser beam of a wavelength of 390 to 420 nm for reproducing data, and projecting the laser beam of a wavelength of 390 to 420 nm for reproducing data onto the recording layer via the light transmission layer, thereby reproducing data recorded in the recording layer,

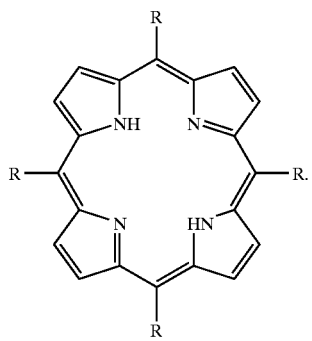

(1)

wherein R in the general formula (1), at each occurrence, is independently selected from the group consisting of

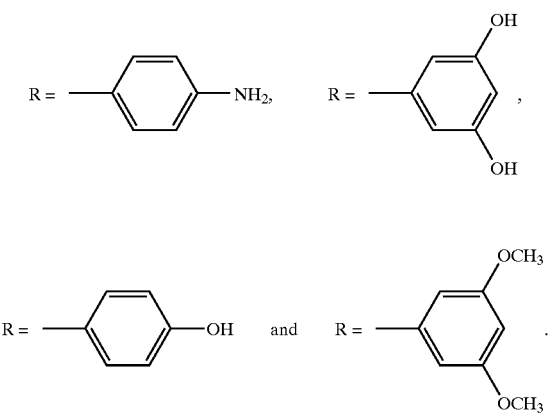

* * * * *